(12) United States Patent
Chatterjee et al.

(10) Patent No.: US 6,322,824 B1
(45) Date of Patent: Nov. 27, 2001

(54) USE OF HYPERFORIN AND HYPERFORIN-CONTAINING EXTRACTS IN THE TREATMENT OF DEMENTIA DISEASES

(75) Inventors: Shyam Sunder Chatterjee; Clemens Erdelmeier; Michael Nöldner, all of Karlsruhe (DE)

(73) Assignee: Willmar Schwabe GmbH & Co., Karlsruhe (DE)

( * ) Notice: Subject to any disclaimer, the term of this patent is extended or adjusted under 35 U.S.C. 154(b) by 0 days.

(21) Appl. No.: 09/622,191

(22) PCT Filed: Feb. 4, 1999

(86) PCT No.: PCT/EP99/00730

§ 371 Date: Aug. 11, 2000

§ 102(e) Date: Aug. 11, 2000

(87) PCT Pub. No.: WO99/40905

PCT Pub. Date: Aug. 19, 1999

(30) Foreign Application Priority Data

Feb. 13, 1998 (DE) ............................... 198 05 946

(51) Int. Cl.$^7$ .......................... A61K 35/78; A61K 31/05; A01N 31/08
(52) U.S. Cl. ...................... 424/730; 514/729; 514/730; 514/731; 514/732
(58) Field of Search ................ 424/195.1, 730; 514/729–732

(56) References Cited

U.S. PATENT DOCUMENTS

| | | | |
|---|---|---|---|
| 4,713,376 | * 12/1987 | Kuzuya | 514/78 |
| 5,733,926 | * 3/1998 | Gorbach | 514/456 |
| 6,117,855 | * 9/2000 | Carlson et al. | 514/90 |
| 6,159,986 | * 12/2000 | Altman | 514/295 |

FOREIGN PATENT DOCUMENTS

| | | |
|---|---|---|
| 19619512 | 7/1997 | (DE) . |
| 0599307A | 11/1993 | (EP) . |
| 04210642 | 7/1992 | (JP) . |
| 9713489 | 4/1997 | (WO) . |
| WO 00/57707 | * 10/2000 | (WO) . |

OTHER PUBLICATIONS

Schmidt et al. Fortschritte der Medizin, vol. 111, No. 19, pp. 37–40, abstract enclosed, 1993.*
Schmidt et al. Therapiewoche, vol. 45, No. 2, pp. 106–112, abstract enclosed, 1995.*
Kumar et al. J. Ethnopharmacol. vol. 72, No. 1–2, pp. 119–128, abstract enclosed, Sep. 2000.*
Buxbaum, Joseph D., et al., Processing of Alzheimer β/A4 amyloid precursor protein: Modulation by agents that regulate protein phosphorylation; Proc. Natl. Acad. Sci, USA, vol. 87, pp. 6003–6006 (Aug., 1990).

Chatterjee, Shyam Sunder, et al., Hyperforin and Hypericun Extract: Interactions with some neurotransmitter systems (abstract); $2^{nd}$ International Congress on Phytomedicine, (1996).
Frohlich, W., Nootropika: BGA verlangt Therapie–Verbund, Hirnleistungsstorungen–Erstattungsfahigkeit, Pharmakotherapie fur die Praxis, p. 48 (1994).
Games, Dora, et al., Alzheimer–type neuropathology in transgenic mice overexpressing V717F β–amyloid precursor protein; Nature, vol. 373, pp. 523–527 (Feb., 1995).
Giacobini, Ezio, Cholinomimetic Therapy of Alzheimer Disease: Does It Slow Down Deterioration?; Int Acad Biomed Drug Res. Basel, Karger, vol. 7, pp. 51–57 (1994).
Herberhold, C., Pflanzliche Arzneien bessern den Score im Hirnleistungstest, Fortschritte der Medizin, Bd 111, Nr. 6, p. 50 (1993).
Hsiao, Karen, et al., Correlative memory Deficits, Aβ Elevation, and Amyloid Plaques in Transgenic Mice; Science, vol. 274, pp. 99–102 (Oct., 1996).
Johnson, D., et al., Effects of Hypericum Extract LI 160 Compared with Maprotiline on Resting EEG and Evoked Potentials in 24 Volunteers, Journal of Geriatric Psychiatry and Neurology, vol. 7, Suppl. 1, pp. S44–S46 (Oct., 1994).
Lamb, Bruce T., Presenilins, amyloid–β and Alzheimer's disease, Nature Medicine, vol. 3, n.1; pp. 28–29 (Jan., 1997).
Lehrl, S., et al., Psychometrische Messung der Leistungskapazitat unter antidepressiver Therapie mit Johanniskraut–Extrakt, Nervenheilkunde 1991: pp. 10:313–315.
Linde, Klaus, St. John's wort for depression—an overview and meta–analysis of randomised clinical trials, BMJ, vol. 313, pp. 253–258 (1996).
Mendla, Klaus,; Die Alzheimer–Krankheit: neue Ansatz in der Pharmakotherapie, PZ Titel, Nr 5 141, pp. 11–16 (Feb., 1996).
Nitsch, Roger M., et al., Release of Alzheimer Amyloid Precursor Derivatives Stimulated by Activation of Muscarinic Acetylcholine Receptors; Science, vol. 258, pp. 304–307 (Oct., 1992).
Scheuner, D., et al., Secreted amyloid β–protein similar to that in the senile plaques of Alzheimer's disease is increased in vivo by the presenilin 1 and 2 and APP mutations linked to familial Alzheimer's disease; Nature Medicine, vol. 2, n.8, pp. 864–870 (Aug., 1996).
Schulz, V., et al., Klinische Studien mit Psycho–Phytopharmaka, Zeitschrift fur Phytotherapie, vol. 18(3), pp. 141–154 (1997).

* cited by examiner

Primary Examiner—Christopher R. Tate
(74) Attorney, Agent, or Firm—Frost Brown Todd LLC

(57) ABSTRACT

The invention relates to the use of hyperforin and hyperforin-containing extracts of *Hypericum perforatum L.* (St. John's wort) in the treatment and prophylaxis of dementia diseases, including Alzheimer's disease, as well as the use of hyperforin and hyperforin-containing extracts for the preparation of a medicament for the treatment and prophylaxis of such dementia diseases.

6 Claims, 2 Drawing Sheets

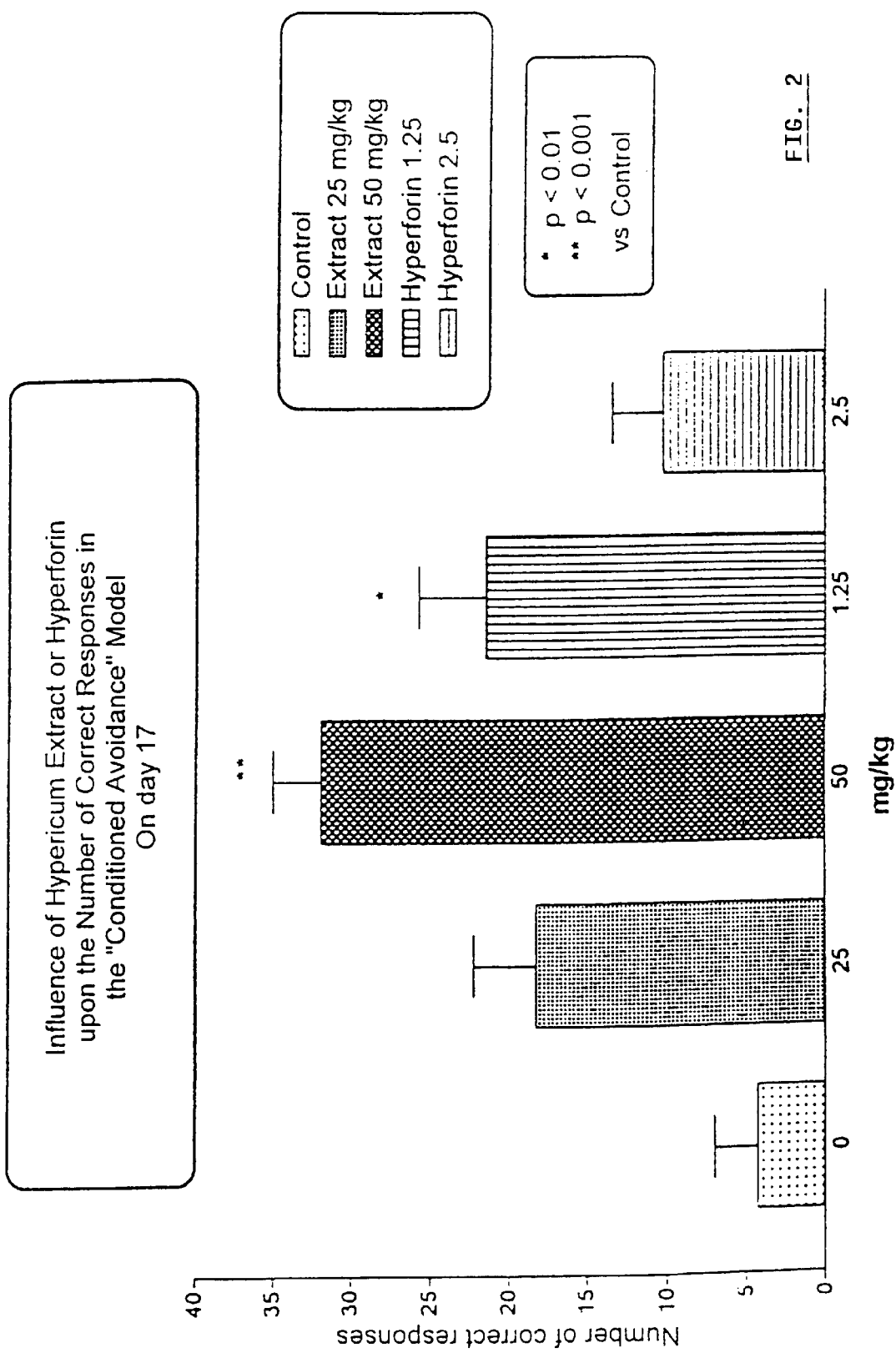

USE OF HYPERFORIN AND HYPERFORIN-CONTAINING EXTRACTS IN THE TREATMENT OF DEMENTIA DISEASES

The invention relates to the use of hyperforin and hyperforin-containing extracts of *Hypericum perforatum L.* (St. John's wort) in the treatment and prophylaxis of dementia diseases such as for example Alzheimer's disease.

The phloroglucin derivative hyperforin of the following structural formula

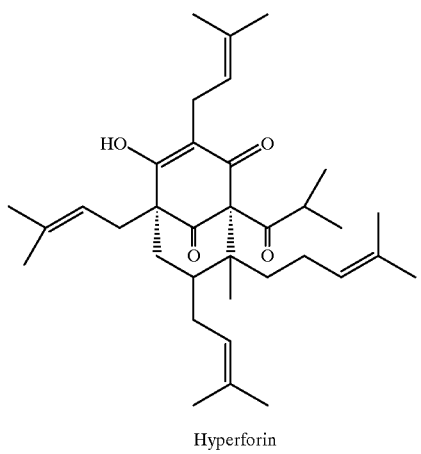

Hyperforin is one of the main constituents of St. John's wort. Since the substance is chemically unstable, its content decreases upon drying of the fresh plant. With rapid drying and under gentle conditions, the St. John's wort drug still contains hyperforin in a high concentration which is comparable with the content of fresh plants.

Hypericum extracts have been used for many years or the treatment of depression and psychovegetative disorders (cf. Linde et al., BMJ, Vol. 313, pp. 253–258, (1996)). A method of preparing hypericum extracts is described in the German Patent 196 19 512, which [contain] a stable [hyperforin content of at least 2%][1].

[1] N. B. The text corresponding to the words in square brackets has been omitted from the PCT application as filed.

Dry extracts of hypericum and methods of preparing them, which are poor in.

Dry extracts of hypericum and methods of preparing them, which are poor in hypericin but have a higher content of hyperforin than the vegetable starting material, are known from EP-A-0 599 307. These extracts have a strongly serotonin-antagonistic effect, and they are used for the preparation of medicines with a psychovegetative and anti-depressive effect. These extracts are used for the treatment of anxiety disorders, nervous agitation, migraines, gastrointestinal disorders and vomiting. In addition, for various preparations, which contain a hypericum extract alone or in combination with other substances, many applications are described in the fields of medicine and cosmetics. In particular, anti-viral and anti-bacterial effects are also known. In this way, the use of hypericum extracts for the treatment of viral diseases, in particular HIV, is known from WO 97/22354, while anti-bacterial effects and the use of ointments containing hypericum extract for the prevention of diseases transmissible through sexual inter-course are described in the Russian Patent RU-C1-2 031 645.

In investigations involving experiments on animals a significant influence upon cognitive functions by hyperforin and hyperforin-containing extracts of *Hypericum perforatum L.* has now surprisingly been found. Such an effect has not been described previously either for hyperforin or for hyperforin-containing extracts and, on the basis of the previously known pharmacological and clinical effects, was also not expected. Within the scope of the present invention an effect upon the memory capacity by a hyperforin-rich hypericum extract and by hyperforin itself has been found for the first time. Hyperforin and hyperforin-containing extracts can thus be used for the therapy of neurological disorders which accompany dementia.

Dementia is defined as a significant reduction in the intellectual capacity which appears as a reduction in the memory and the power to reason and is linked to a deterioration in the personal activities of daily life. Large-scale autopsy statistics and clinical-epidemiological investigations show that, at approximately 60%, neurodegenerative diseases are the most common cause of dementia. After that, approximately 20% of cases are the so-called vascular forms of dementia and a further 20% are other causes (cf. Rösler et al., *Fortschr. Med.* 114, pp. 351–356 (1996)). No generally recognized method of therapy for dementia diseases has existed until now, so that treatment has had to be restricted to the amelioration of the clinical symptoms.

Alzheimer's dementia or Alzheimer's disease is an illness which starts insidiously and which is characterized by initial forgetfulness, increasing lapses of memory and the loss of further cognitive abilities. It ends with the total intellectual decay and personality loss of the patient. A satisfactory causally orientated therapy of this illness has not previously been available (cf. K. Mendla, "*Die Alzheimer-Krankheit: Neue Ansätze in der Pharmakotherapie*" [Alzheimer's Disease: New starting points in pharmacotherapy], *Pharm. Zeitung* 141, pp. 351–356 (1996)). Alzheimer's dementia is treated with acetylcholinesterase inhibitors in order to increase the quantity of acetylcholine available in the brain. This treatment leads to a number of undesired side-effects which do not permit permanent therapy (cf. Shvaloff et al., *Psychopharmacology Bulletin*, Vol. 32, pp. 343–352 (1996)).

The object of the invention is therefore to make available substances having an anti-dementia effect and compositions containing such substances, which have fewer side-effects than the medicaments used hitherto for this indication.

The subject of the invention is therefore the use of hyperforin and hyperforin-containing extracts of *Hypericum perforatum L.* (St. John's wort) in the treatment and prophylaxis of dementia diseases, including Alzheimer's disease, vascular dementia and mixed forms of dementia, and thus the use of hyperforin and hyperforin-containing extracts as a medicament for the treatment of diseases which accompany a disorder of the memory or learning ability, as well as the use of hyperforin and hyperforin-containing extracts of St. John's wort in the preparation of a medicament for the treatment and prophylaxis of dementia diseases, in particular Alzheimer's disease, vascular dementia and mixed forms of dementia.

Without wishing to be bound by a specific theory, the use of hyperforin and hyperforin-containing extracts appears to have a causally therapeutic starting point, since it has surprisingly been found that hyperforin and the extracts named are powerful stimulators of the protein kinase C$\gamma$. This protein kinase C$\gamma$ activates the $\alpha$-secretase, which in turn prevents the occurrence of the pathogenic amyloid A$\beta$. A special advantage of hyperforin and hyperforin-containing extracts is thus that not only do they prevent the formation of amyloid A$\beta$ in a desired manner, but in addition it is possible to combat effectively the psychiatric attendant symptoms, such as anxiety, depression and other psychovegetative disorders, which frequently occur in dementia diseases, in particular Alzheimer's.

BRIEF DESCRIPTION OF THE DRAWINGS

FIG. 2—shows the influence of Hypericum extract or Hyperforin on cognitive effect in animal models on day 17.

Figure 1:
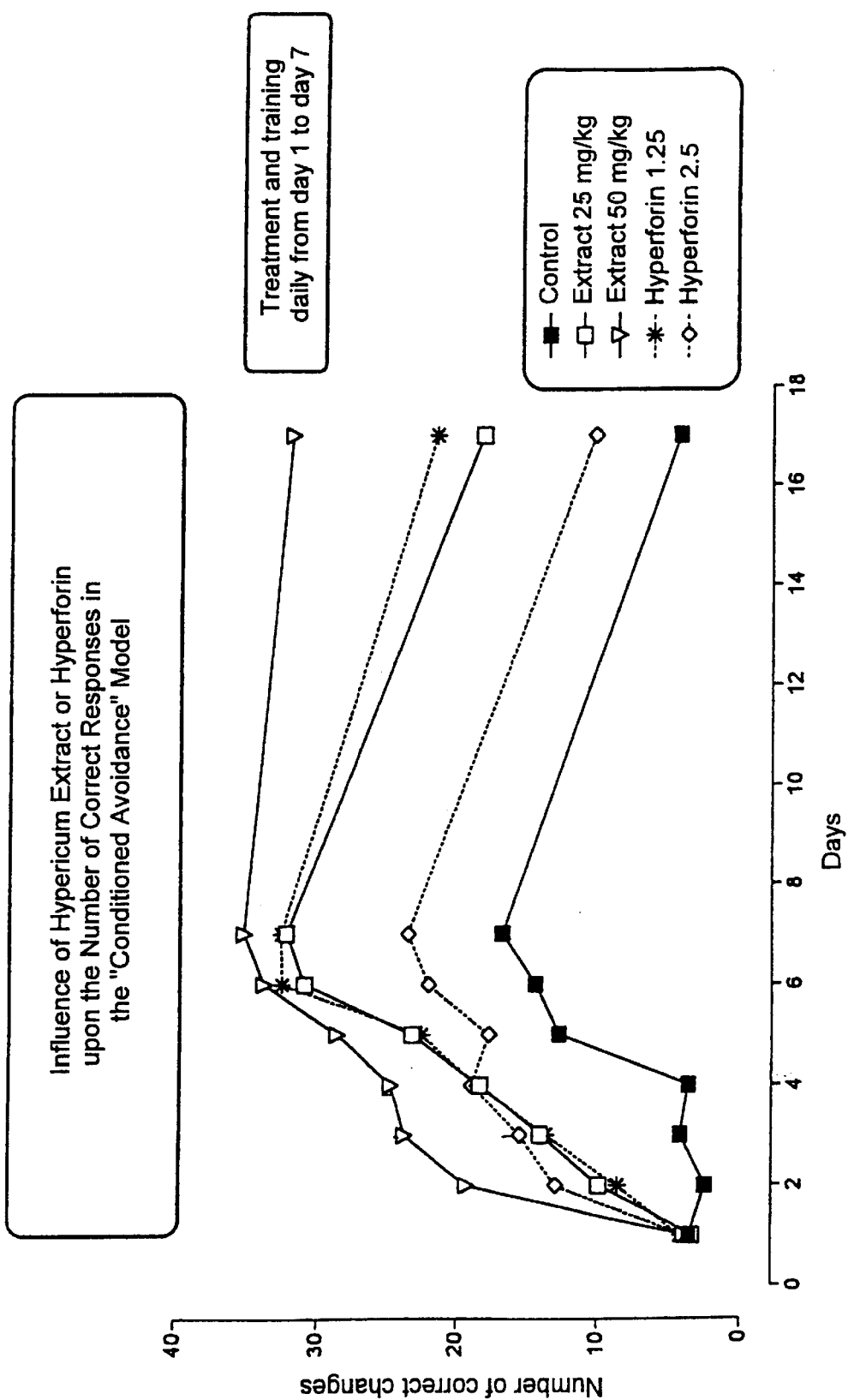
FIG. 1—shows the influence of Hypericum extract or Hyperforin on cognitive effect in animal models from days 1–7.

A hyperforin-containing extract which can be used according to the invention was obtained as follows:

30 kg of dried, ground crude herbal drug of St. John's wort were introduced into a high-pressure extraction unit and extraction was carried out at $280 \times 10^5$ Pa (280 bar) and at 40° C. with carbon dioxide. During the extraction, 30 kg of $CO_2$ per kilogram of the drug were introduced. After the extraction, the pressure was reduced to $60 \times 10^5$ Pa (60 bar), the extract being precipitated. The extract was removed from the apparatus and was separated from jointly extracted water by heating to approximately 45° C. 1.25 kg of extract with a hyperforin content of 34.5% was obtained. In order to stabilize the hyperforin, 500 mg of ascorbic acid stearate were added to the warm extract.

In order to isolate hyperforin from the extract obtained in this way, the following steps are carried out:

31 g of the extract obtained in accordance with the method described above were dissolved with stirring, under a nitrogen atmosphere and with protection from light in 3 litres of n-heptane which was saturated with methanol. The extract solution obtained was then extracted by shaking once with 1.5 litres of methanol which had been saturated with n-heptane, and three times each with one litre of the same solvent. The methanol phases were combined and were dried at a water-bath temperature of a maximum of 45° C. on a rotary evaporator. Subsequent drying took place overnight in a vacuum-drying cabinet at room temperature. In this way 20.14 g of methanol phase were obtained.

The total quantity of methanol phase was dissolved in 100 ml of methanol. The stock solution obtained in this way was used for preparative high-pressure liquid chromatography (HPLC): it was de-gassed for approximately 2 minutes in an ultra-sound bath, stored in an amber glass under a nitrogen atmosphere at −18° C. and subjected to preparative HPLC. 3.7 ml of the stock solution were used for each preparative HPLC separation, and this corresponds to a quantity of material of 745 mg. The conditions of the preparative HPLC were as follows:

eluent: 88% by volume of methanol, purest quality detection: 270 nm flow: 90 ml/min column: Eurospher 100-C18, 7 µm, ID 32 mm.

The hyperforin peak was collected from each individual preparative separation. The HPLC eluates containing hyperforin were first stored at −18° C. Then they were combined and continuously concentrated on the rotary evaporator at a maximum of 45° C. of a water-bath temperature, under light protection and with nitrogen gassing of the storage vessel. These concentrates were flushed with the aid of methanol into amber glasses and were stored under a nitrogen atmosphere until the final combining at −18° C. After drawing off the methanol and after a high-vacuum drying, 9.4 g of hyperforin were obtained, which was characterized by UV, IR and $^1$H-NMR and $^{13}$C-NMR spectra.

As an animal model for demonstrating the cognitive effect of hyperforin and the hyperforin-containing extract obtained in accordance with the method described above, the so-called "conditioned avoidance" model was selected.

In this model a closed cage of plastics material, the "conditioned avoidance box", was used, which is separated in the middle by a partition wall into two chambers or compartments of equal size. A door, which can be opened and closed by an automatic control, is provided in the middle of the partition wall. The base of the two chambers comprises an electrically conductive grating. A lamp and a loudspeaker, by way of which light and auditory signals can be emitted, are provided on the walls of each chamber.

An individual rat is placed for training in the right-hand compartment of the box in each case, the door in the partition wall remaining closed. After the rat has had 10 minutes to become accustomed to the new surroundings, an automated programmed begins with the opening of the door. After 20 seconds a combined sound-light signal is emitted for 3 seconds in the chamber in which the rat is present (conditioned stimulus). If the rat remains in the chamber despite the stimulus, 3 seconds of continuous current stimulation occurs by way of the grating bars (unconditioned stimulus). A new cycle then begins. If the rat changes into the opposite chamber before or during the conditioned stimulus it avoids the current stimulation, and the new cycle begins in the other chamber. This procedure is repeated in the same manner on seven consecutive days. There is then a pause of 10 days, during which neither treatment nor training takes place. On the 17th day of the test the animals are placed in the box for a last time, but with the difference that current stimulation is no longer applied.

The rats learn from the daily training programmed that they can avoid the current stimulation by changing the compartments (avoidance behaviour). Substances which improve the learning or memory functions, lead to a more rapid learning of the avoidance behaviour and thus to a smaller number of electric shocks.

Daily oral applications of 25 or 50 mg/kg hypericum extract as well as 2.5 or 5 mg/kg of pure hyperforin lead to a significantly more rapid learning of the avoidance behaviour. In the test arrangement described, this effect may be seen in a significantly higher number of correct avoidance reactions during the seven-day treatment and training phase (cf. FIG. 1). The learned behaviour is forgotten less quickly by the animals treated with hypericum extract or with hyperforin, and this is evident in the reaction of the animals on the 17th day of the test after the ten-day pause in the treatment and training (cf. FIG. 2).

The graphs reproduced in FIG. 1 indicate the number of the correct changes of the test animals from one compartment into the other from the 1st day to the 7th day and—after the ten-day pause—on the 17th day, both for untreated test animals and for test animals which were given 25 mg/kg or 50 mg/kg hypericum extract p.o. daily, and those test animals which were given 1.25 or 2.5 mg/kg pure hyperforin p.o. daily. In this case it is clear that pure hyperforin is less effective than hypericum extract in a dose of 50 mg/kg.

The number of the correct responses of the test animals on the 17th day is given once more in a different graphic form in FIG. 2.

What is claimed is:

1. A method of treating dementia diseases by administering to a patient in need of such treatment a safe and effective amount of a material selected from hyperforin, and a hyperforin-containing extract of *hypericum perforatum L* (St. John's Wort).

2. The method according to claim 1 for the treatment for Alzheimer's disease.

3. The method according to claim 1 for the treatment of vascular dementia.

4. The method according to claim 1 for the treatment of mixed forms of dementia.

5. The method according to one of claims 1 and 2–4 wherein the extract contains at least 2% by weight of hyperforin.

6. The method according to one of claims 1 and 2–5 wherein the hyperforin is stabilized by the addition of a stabilizer.

* * * * *

UNITED STATES PATENT AND TRADEMARK OFFICE
CERTIFICATE OF CORRECTION

PATENT NO.   : 6,322,824 B1                                               Page 1 of 1
DATED        : November 27, 2001
INVENTOR(S)  : Shyam Sunder Chatterjee, Clemens Erdelmeier and Michael Noldner It is certified that error appears in the above-identified patent and that said Letters Patent is hereby corrected as shown below:

<u>Column 4,</u>
Line 63, "2-5" should read -- 2-4 --

Signed and Sealed this

Second Day of July, 2002

Attest:

Attesting Officer

JAMES E. ROGAN
*Director of the United States Patent and Trademark Office*